(12) United States Patent
Blum et al.

(10) Patent No.: US 12,154,665 B2
(45) Date of Patent: *Nov. 26, 2024

(54) SYSTEM AND METHOD FOR CREATION OF PERSISTENT PATIENT IDENTIFICATION

(71) Applicant: IQVIA Inc., Parsippany, NJ (US)

(72) Inventors: Christopher Blum, Wynnewood, PA (US); Geoff Wall, Newtown, PA (US); John Giannouris, Flemington, NJ (US)

(73) Assignee: IQVIA Inc., Parsippany, NJ (US)

( * ) Notice: Subject to any disclaimer, the term of this patent is extended or adjusted under 35 U.S.C. 154(b) by 577 days.

This patent is subject to a terminal disclaimer.

(21) Appl. No.: 17/461,190

(22) Filed: Aug. 30, 2021

(65) Prior Publication Data
US 2021/0398626 A1    Dec. 23, 2021

Related U.S. Application Data

(63) Continuation of application No. 16/827,553, filed on Mar. 23, 2020, now Pat. No. 11,133,093, which is a continuation of application No. 14/711,503, filed on May 13, 2015, now Pat. No. 10,600,506.

(51) Int. Cl.
*G16H 10/60*    (2018.01)
*G06F 21/62*    (2013.01)

(52) U.S. Cl.
CPC ......... *G16H 10/60* (2018.01); *G06F 21/6254* (2013.01); *G06Q 2220/00* (2013.01)

(58) Field of Classification Search
None
See application file for complete search history.

(56) References Cited

U.S. PATENT DOCUMENTS

| | | |
|---|---|---|
| 10,600,506 B2 | 3/2020 | Blum et al. |
| 11,133,093 B2 | 9/2021 | Blum et al. |
| 2003/0039362 A1 | 2/2003 | Califano |
| 2005/0165623 A1 | 7/2005 | Landi |
| 2006/0026156 A1* | 2/2006 | Zuleba ............... G06F 21/6227 707/999.005 |
| 2007/0192139 A1* | 8/2007 | Cookson ............... G16H 10/60 705/3 |

(Continued)

*Primary Examiner* — Devin C Hein
(74) *Attorney, Agent, or Firm* — Fish & Richardson P.C.

(57) ABSTRACT

Methods, systems, and apparatus, including computer programs encoded on computer storage media, for creating source-specific, persistent patient identifiers for healthcare service providers. One method includes accessing a record of healthcare data, wherein the record includes patient identifying information (PII) associated with one or more persons to whom the healthcare data pertains. The portions of PII included in the accessed record of healthcare data are extracted from the accessed record and encrypted. Based on one or more business rules, one or more hashed tokens are created by applying one or more hashing functions to the extracted portions of PII. A source-specific identifier is received, the source-specific identifier having been encoded in a manner specific to an organization associated with the computer system and having been encoded with reference to the one or more hashed tokens. An association is stored between the source-specific identifier and the accessed record of healthcare data.

22 Claims, 5 Drawing Sheets

(56) References Cited

U.S. PATENT DOCUMENTS

| | | |
|---|---|---|
| 2008/0147554 A1 | 6/2008 | Stevens |
| 2010/0034376 A1* | 2/2010 | Okuizumi ............ G06F 21/6254 380/44 |
| 2015/0074409 A1* | 3/2015 | Reid ................... G06F 21/6218 713/171 |
| 2020/0294635 A1 | 9/2020 | Blum |

* cited by examiner

SYSTEM AND METHOD FOR CREATION OF PERSISTENT PATIENT IDENTIFICATION

CROSS REFERENCE TO RELATED APPLICATIONS

This application is a continuation of U.S. application Ser. No. 16/827,553 filed Mar. 23, 2020, which is a continuation of U.S. application Ser. No. 14/711,503, filed on May 13, 2015, now U.S. Pat. No. 10,600,506, the entire contents of which are hereby incorporated by reference in its entirety.

BACKGROUND

An increasing amount of patient healthcare data regarding diagnosis and treatment is being electronically entered and recorded. For example, a healthcare provider may electronically submit healthcare data for the purpose of receiving payment for services rendered. The healthcare data may be transmitted amongst healthcare providers, clearinghouses and/or providers of electronic data interchange, and/or insurance companies. Such healthcare data may include standardized codes to describe diagnoses made, services performed, or products used.

However, regulations in various countries, such as the Health Insurance Portability and Accountability Act of 1996 (HIPAA) in the U.S., restrict covered entities from disclosing protected health information ("PHI"). The disclosure of PHI is regulated because it is healthcare data with personally identifiable information ("PII"). Many data sources would be considered covered entities because the data sources produce information that may contain PHI, and PHI through its associated PII can be used to positively identify the patient with whom the healthcare data is related.

SUMMARY

The present disclosure relates to computer-implemented methods, software, and systems for creating source-specific, persistent patient identifiers for healthcare service providers. In one aspect, a system includes a first computer system comprising one or more first processors and one or more first storage devices, and a second computer system comprising one or more second processors and one or more second storage devices. The one or more first storage devices store instructions that, when executed by the one or more first processors, cause the one or more first processors to perform operations including: accessing a record of healthcare data, wherein the record includes patient identifying information (PII) associated with one or more persons to whom the healthcare data pertains; extracting portions of PII included in the accessed record of healthcare data; encrypting the extracted portions of PII; based on one or more business rules, creating one or more hashed tokens by applying one or more hashing functions to the extracted portions of PII; transmitting the one or more hashed tokens; receiving, in response to the transmission of the one or more hashed tokens, a source-specific identifier, the source-specific identifier having been encoded in a manner specific to an organization associated with the first computer system; and storing an association between the source-specific identifier and the accessed record of healthcare data. The one or more second storage devices store instructions that, when executed by the one or more second processors, cause the one or more second processors to perform operations comprising: receiving, from the first computer system, the one or more hashed tokens; based on the received one or more hashed tokens, creating a source-specific identifier that is encoded in a manner specific to an organization associated with the first computer system; and transmitting the created source-specific identifier to the first computer system. In some implementations, the first and second computer systems may each be located and/or operated separately from each other.

Other implementations of these aspects include corresponding methods, apparatus, and computer programs recorded on one or more computer storage devices, each configured to perform the actions of the system. A system of one or more computers can be configured to perform particular operations or actions by virtue of having software, firmware, hardware, or a combination of software, firmware, or hardware installed on the system that in operation causes or causes the system to perform the actions. One or more computer programs can be configured to perform particular operations or actions by virtue of including instructions that, when executed by a data processing apparatus, cause the apparatus to perform the actions. A method can be implemented to carry out one or more of the operations performed by the system.

These and other aspects may each optionally include one or more of the following features. For example, the second computer system may be further configured to: compare the received one or more hashed tokens to one or more previously received hashed tokens; based on the comparison of the received one or more hashed tokens to the one or more previously received hashed tokens, identify an indexing tag related to the received one or more hashed tokens; and encode the indexing tag in a manner specific to the organization associated with the first computer system.

Additionally or alternatively, the first computer system may be configured to: de-identify the accessed record of healthcare data; and transmit the de-identified record of healthcare data. Additionally or alternatively, the system may further include a third computer system comprising one or more third processors and one or more third storage devices. In these implementations, the one or more third storage devices may store instructions that, when executed by the one or more third processors, cause the one or more third processors to perform operations comprising: receiving, from the second computer system, the identified indexing tag; receiving the de-identified record of healthcare data; and storing an association between the received indexing tag and the received de-identified record of healthcare data.

Additionally or alternatively, the first computer system may be configured to: search for one or more other records of healthcare data with which the source-specific identifier has been previously associated; based on the search, identify one or more other records of healthcare data with which the source-specific identifier has been previously associated; and store an association between the accessed record of healthcare data and the identified one or more other records of healthcare data with which the source-specific identifier has been previously associated.

The details of one or more implementations of the subject matter of this specification are set forth in the accompanying drawings and the description below. Other features, aspects, and advantages of the subject matter will become apparent from the description, the drawings, and the claims.

DESCRIPTION OF DRAWINGS

Like reference numbers and designations in the various drawings indicate like elements.

DETAILED DESCRIPTION

Figure 1:
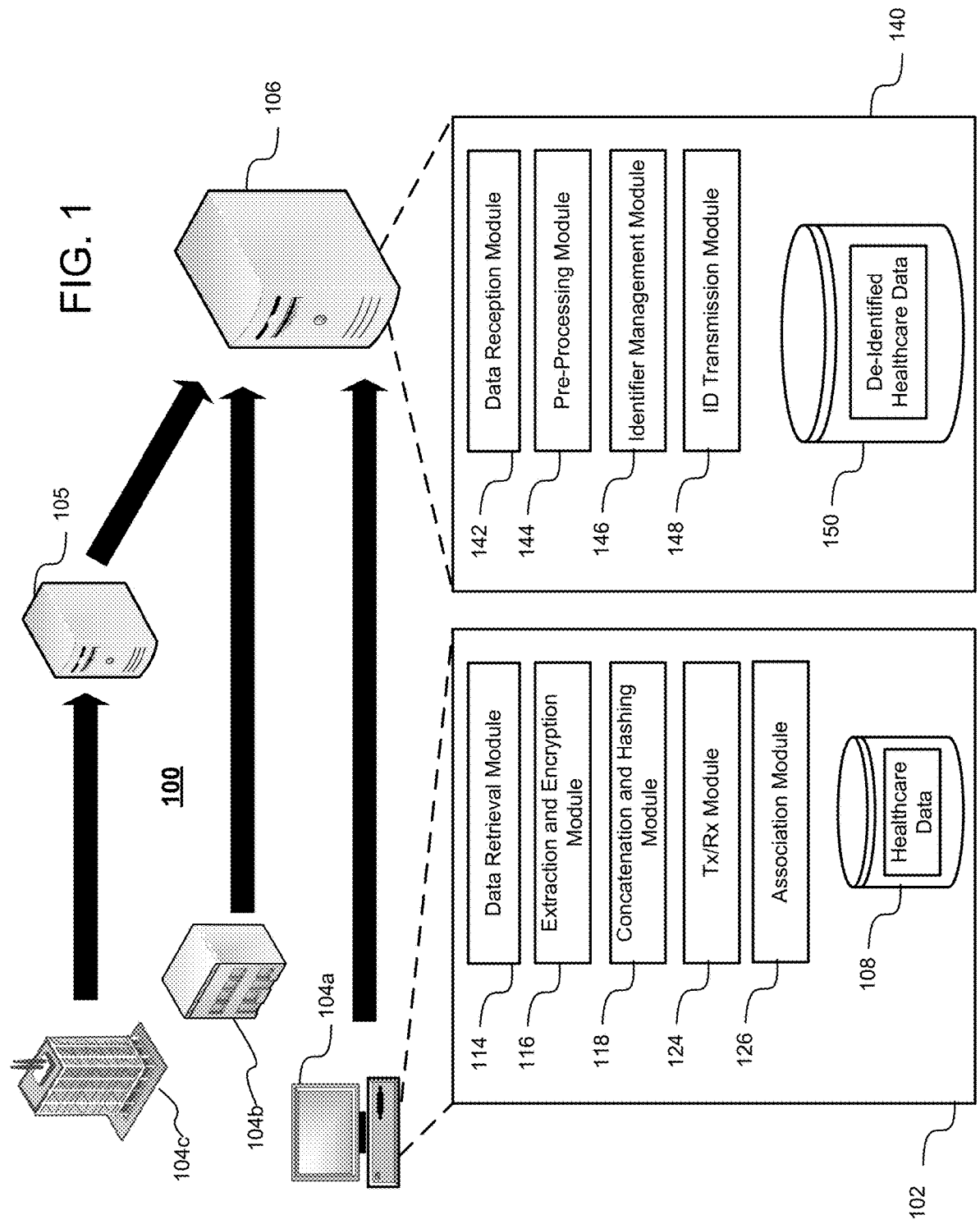
FIG. 1 is a block diagram illustrating an example system for creating source-specific, persistent patient identifiers.

This disclosure generally describes computer-implemented methods, software, and systems for creating source-specific, persistent patient identifiers for healthcare professionals and/or organizations. For illustration purposes, the various implementations described herein will be described with regard to patient healthcare data that may be created, stored, or transmitted by healthcare professionals (e.g., doctors, nurses, technicians, and/or pharmacists), medical facilities (e.g., doctor's offices, hospitals, clinics, and/or nursing homes), healthcare service providers (e.g., insurance companies), and/or retail outlets (e.g., pharmacies). However, the described persistent patient identification system is equally applicable to the anonymous identification of all types of private, personal data and the entities that create, store, or transmit that data. Additionally or alternatively, the described persistent patient identification system may be configured to facilitate data de-identification in other types of software or hardware (e.g., advertising software or hardware).

In some implementations, the described persistent patient identification system is configured to protect and de-identify healthcare data by converting elements of PII into one or more anonymous linking tokens that facilitate tracking and analysis of the healthcare data by uniquely identifying the healthcare data while preserving the anonymity of the individual associated with the healthcare data. For example, the described persistent patient identification system may form the anonymous linking tokens from predetermined portions of PII contained in a record of healthcare data and replacing the PII in that record of healthcare data with the anonymous linking tokens. The healthcare data is "de-identified" by removing all information considered to be PII. The anonymous linking tokens are then appended to the healthcare data. The use of multiple anonymous linking tokens based on varying combinations of PII increases the likelihood of linking the de-identified healthcare data with other de-identified healthcare data associated with the same individual patient.

The anonymous linking tokens allow for linking or associating of healthcare data for a particular person even though the healthcare data has no direct identifiers, comes from different data sources, and was created at different times. In some implementations, the de-identified data with the appended anonymous linking tokens is sent to one or more data warehouses that can join several data files at the de-identified patient-specific level. At the one or more data warehouses, the anonymous linking tokens can be replaced with or augmented by an indexing tag. By replacing the anonymous linking tokens, which is based on portions of PII, with the indexing tag, the healthcare data is further de-identified because it contains no PII, and the anonymous linking tokens, which are based on portions of PII, are replaced by the indexing tag. Data can then be linked (i.e., associated with other data related to the same person) and clustered without using PII or any data based on PII. By de-identifying the healthcare data in this manner, the persistent patient identification system supports the detailed analysis of patient-level healthcare data while complying with regulations governing the storage and transmission of patient healthcare data.

In some implementations, the persistent patient identification system includes one or more mechanisms to assist healthcare professionals, medical facilities, healthcare service providers, and/or retail outlets from which de-identified healthcare data is received to track a patient even when that patient's information changes. For example, a patient may change health insurance plans for various reasons (e.g., switching jobs, retiring, moving to Medicare, etc.). A health insurance company serving a patient that changes plans may not be able to accurately track a patient's change in plan until after a claim has been submitted on behalf of the patient. Since the patient may not submit an initial claim for an extended period of time after a switch in health insurance plans (e.g., weeks or even months), there may be a relatively long period of time after the patient switches health insurance plans that the health insurance company cannot confirm whether it already has data for the patient from previous plans or whether the patient is actually new to health insurance company. Since the above-described one or more data warehouses anonymously tracks patients across many, if not all, healthcare professionals, medical facilities, healthcare service providers, and/or retail outlets with which the patient interacts through the anonymous linking tokens and indexing tags, the one or more data warehouses may have the information necessary to assist the health insurance company in determining whether a patient changing health insurance plans is a patient who has previously had a plan with the health insurance company or is a new patient.

One mechanism by which the persistent patient identification system may be configured to assist healthcare professionals, medical facilities, healthcare service providers, and/or retail outlets to track a patient even when that patient's information changes is by the use of creating source-specific, persistent patient identifiers. In one implementation, the persistent patient identification system may be configured to receive the above-described one or more anonymous linking tokens from a healthcare professional, medical facility, healthcare service provider, or retail outlet and determine a corresponding indexing tag that is used by the persistent patient identification system to anonymously identify the patient corresponding to the one or more anonymous linking tokens. The persistent patient identification system may encode or encrypt the corresponding indexing tag in a manner specific to the healthcare professional, medical facility, healthcare service provider, or retail outlet from which the one or more anonymous linking tokens were received, creating a source-specific, persistent patient identifier. Because the persistent patient identification system encrypts or encodes the source-specific, persistent patient identifier in a manner specific to each healthcare professional, medical facility, healthcare service provider, or retail outlet from which one or more anonymous linking tokens are received, the persistent patient identification system ensures that the returned source-specific, persistent patient identifier is only useful to that particular healthcare professional, medical facility, healthcare service provider, or retail outlet, thereby protecting the privacy of the patient.

In some implementations, the persistent patient identification system is configured to handle de-identification and source-specific, persistent patient identification in a number of different countries or other geographical regions, complying with the local regulations governing the storage and transmission of patient healthcare data. For example, the persistent patient identification system may be configured to designate various fields with a record of healthcare data as PII for purposes of de-identification depending on the regulations for the relevant jurisdiction(s). Additionally or alternatively, the persistent patient identification system may rely upon different portions of PII in creating the one or more anonymous linking tokens, depending on the regulations for the relevant jurisdiction(s). Additionally or alternatively, the persistent patient identification system may employ varying encryption algorithms depending on the regulations for the relevant jurisdiction(s).

FIG. 1 is a block diagram illustrating an example system for creating source-specific, persistent patient identifiers. The example persistent patient identification system 100 illustrated in FIG. 1 is shown as including a source-side component 102 and a collection-side component 140. Each of the source-side component 102 and collection-side component 140 may be implemented on one or more computers. The implementation shown in FIG. 1 illustrates multiple instances of the source-side component 102, each being implemented across one or more computers. For example, the source-side component 102 may be implemented on a computer 104*a* at a doctor's office, across a computer system 104*b* at a clinic, and/or across a computer system 104*c* at an insurance company. Additionally or alternatively, the source-side component 102 or a portion thereof may also be implemented on one or more computer systems 105 located at one or more trusted third-party intermediaries. The collection-side component 140 may similarly be implemented on one or more computer systems 106 at one or more sites that collect and analyze de-identified healthcare data.

Though the persistent patient identification system 100 is illustrated as including a source-side component 102 and a collection-side component 140, the persistent patient identification system 100 may be logically divided into more or fewer components and implemented at more or fewer locations while still performing the same or similar processing functions, as will be described in greater detail below. For example, where regional privacy laws permit and proper agreements are in place, the source-side component 102 may be implemented entirely at trusted third party intermediaries to which various sources of healthcare data (e.g., healthcare professionals, medical facilities, healthcare service providers, and/or retail outlets) send healthcare data using secure communication means (e.g., secure FTP).

The source-side component 102 will be described as including one or more storage devices 108 that store healthcare data. The stored healthcare data may be input by a user (e.g., a healthcare professional) of the computer or computer system on which the source-side component 102 is implemented. Additionally or alternatively, the stored healthcare data may be received from another computer or computer system. For example, the computer system 104*b* located at a clinic may include multiple computers at which users enter healthcare data. The source-side component 102 may be implemented on one or more of these multiple computers. For example, in some implementations, each computer at which healthcare data is entered may implement an instance of source-side component 102. Additionally or alternatively, the source-side component 102 may be implemented at one of the multiple computers located at the clinic and the other computers may send input healthcare data to the computer implementing the source-side component 102.

The healthcare data stored in the one or more storage devices 108 is data that pertains to the health, condition, disease, treatment, and other similar information of a particular person. The healthcare data may include personal identifying information (PII) for identifying the person to whom the healthcare data pertains. The healthcare data can include, but is not limited to, diagnoses, patient visit information, drug data, procedure data, prescription specific information, laboratory data, data feeds, test orders, test results, consultant's report, and other similar data related to or associated with the health of a person. In some implementations, the healthcare data may include standardized codes to describe the diagnoses made, services performed, products used, and other relevant information.

For ease of explanation, the following disclosure may refer to healthcare data with regard to a record. However, the term record is not meant to limit the content, format, quantity, or quality of healthcare data or the manner in which it is provided, stored, or processed. Rather, a record is simply being used to refer to a discrete quantity of healthcare data that contains PII identifying one or more persons to whom the healthcare data corresponds. In some implementations, the healthcare data may be provided on a standard form, such as CMS-1500/837p, CMS-1450/uB-92/uB-04/837i, NCPDP 5.1, or other similar forms. However, the healthcare data may be provided or stored in one or more data structures that take any standard or non-standard format. In some implementations, for example, the healthcare data may be contained in healthcare insurance claims from pharmacies and physicians. Moreover, the term record does not limit the source of the healthcare data. In some implementations, for example, the healthcare data may be provided directly by a healthcare provider or provided by a central clearinghouse, a payer, a pharmacy benefits manager, or other similar sources of health care data.

The PII contained in the healthcare data may come in various forms. For example, PII may include, but is not limited to, direct identifiers, such as names, elements of addresses, birth dates, social security numbers, insurance policy numbers, and/or license numbers. Additionally or alternatively, PII may include indirect identifiers that may not, on their own, identify a person, but that may, in combination with other information, be used to identify a person. Whether or not one or more portions of healthcare data contained in a record are considered to be PII may be dictated by legal rules and regulations, privacy policies, and/or the individuals and organizations that create, provide, store, or process healthcare data.

In some implementations, the healthcare persistent patient identification system 100 is provided with business rules that identify which portions of healthcare data contained in a record are considered to be PII and how to handle that PII. These PII business rules may be static or dynamic and may take any form. The term business rule is not meant to be limiting, and simply refers to any data, logic, or instruction that informs the handling of PII. The PII business rules may, for example, be provided to the persistent patient identification system 100 by an individual or entity that designs, builds, implements, operates, and/or maintains the persistent patient identification system 100. For example, the PII business rules may be hardcoded into the persistent patient identification system 100 by an individual or entity that designs the persistent patient identification system 100. Additionally or alternatively, the persistent patient identification system 100 may be configured to obtain PII business rules from one or more sources. For example, the persistent patient identification system 100 may be configured to obtain PII business rules or information relevant to PII business rules from government organizations that disseminate information regarding rules, regulations, and/or statutes governing healthcare data.

In some implementations, the record itself may contain data that identifies which portions correspond to PII. Additionally or alternatively, a user or administrator of the persistent patient identification system 100 may identify which portions of a record correspond to PII. For example, a healthcare professional may identify portions of healthcare data as being PII as the healthcare professional enters healthcare data into the healthcare persistent patient identification system 100. In another example, a healthcare professional or other user may designate portions of healthcare data as PII while reviewing previously stored healthcare data.

For illustrative purposes, the source-side component 102 will be described as including a data retrieval module 114, an extraction and encryption module 116, a concatenation and hashing module 118, a transmission/reception module 124, and an association module 126. However, the source-side component 102 may be any computing platform capable of performing the described functions. For example, the source-side component 102 may include one or more computing systems that may include hardware, software, or a combination of both for performing the described functions. Moreover, the data retrieval module 114, extraction and encryption module 116, concatenation and hashing module 118, transmission/reception module 124, and association module 126 may be embodied together or separately in hardware and/or software. Though the data retrieval module 114, extraction and encryption module 116, concatenation and hashing module 118, transmission/reception module 124, and association module 126 will be described as each carrying out certain functionality, the described functionality may be performed by one or more other modules in conjunction with or in place of the described module. In some implementations, the data retrieval module 114, extraction and encryption module 116, concatenation and hashing module 118, transmission/reception module 124, and association module 126 may each be implemented across more than one computer or computer system. For example, in the computer system 104b located at a clinic, each computer included in the computer system 104b may implement one or more of the data retrieval module 114, extraction and encryption module 116, concatenation and hashing module 118, transmission/reception module 124, and/or association module 126 while a single central computer of the computer system 104b may implement the other modules.

For illustrative purposes, the collection-side component 140 will be described as including a data reception module 142, a pre-processing module 144, a identifier management module 146, and an ID transmission module 148. However, the collection-side component 140 may be any computing platform capable of performing the described functions. For example, the collection-side component 140 may include one or more computing systems that may include hardware, software, or a combination of both for performing the described functions. Moreover, the data reception module 142, pre-processing module 144, identifier management module 146, and ID transmission module 148 may be embodied together or separately in hardware and/or software. Though the data reception module 142, pre-processing module 144, identifier management module 146, and ID transmission module 148 will be described as each carrying out certain functionality, the described functionality may be performed by one or more other modules in conjunction with or in place of the described module. In some implementations, the data reception module 142, pre-processing module 144, identifier management module 146, and ID transmission module 148 may each be implemented across more than one computer or computer system. For example, in the computer system 106 located at a collection site, each computer included in the computer system 106 may implement one or more of the data reception module 142, pre-processing module 144, identifier management module 146, and/or ID transmission module 148.

The collection-side component 140 will also be described as including one or more storage devices 150 that store de-identified healthcare data. The one or more storage devices 150 may be configured to store de-identified healthcare data received from one or more source-side components 102. Additionally or alternatively, the one or more storage devices 150 may be configured to store de-identified healthcare data that has been longitudinally linked with previously received de-identified healthcare data. In some implementations, the collection-side component 140 stores the de-identified healthcare data in association with an indexing tag that anonymously identifies the patient to whom the de-identified healthcare data corresponds. The indexing tag may be stored in the same or a different data structure and/or the same or a different storage device as the de-identified healthcare data with which it is associated. Additionally or alternatively, the one or more storage devices 150 may be configured to store one or more reports created based on the stored de-identified healthcare data.

Figure 2:
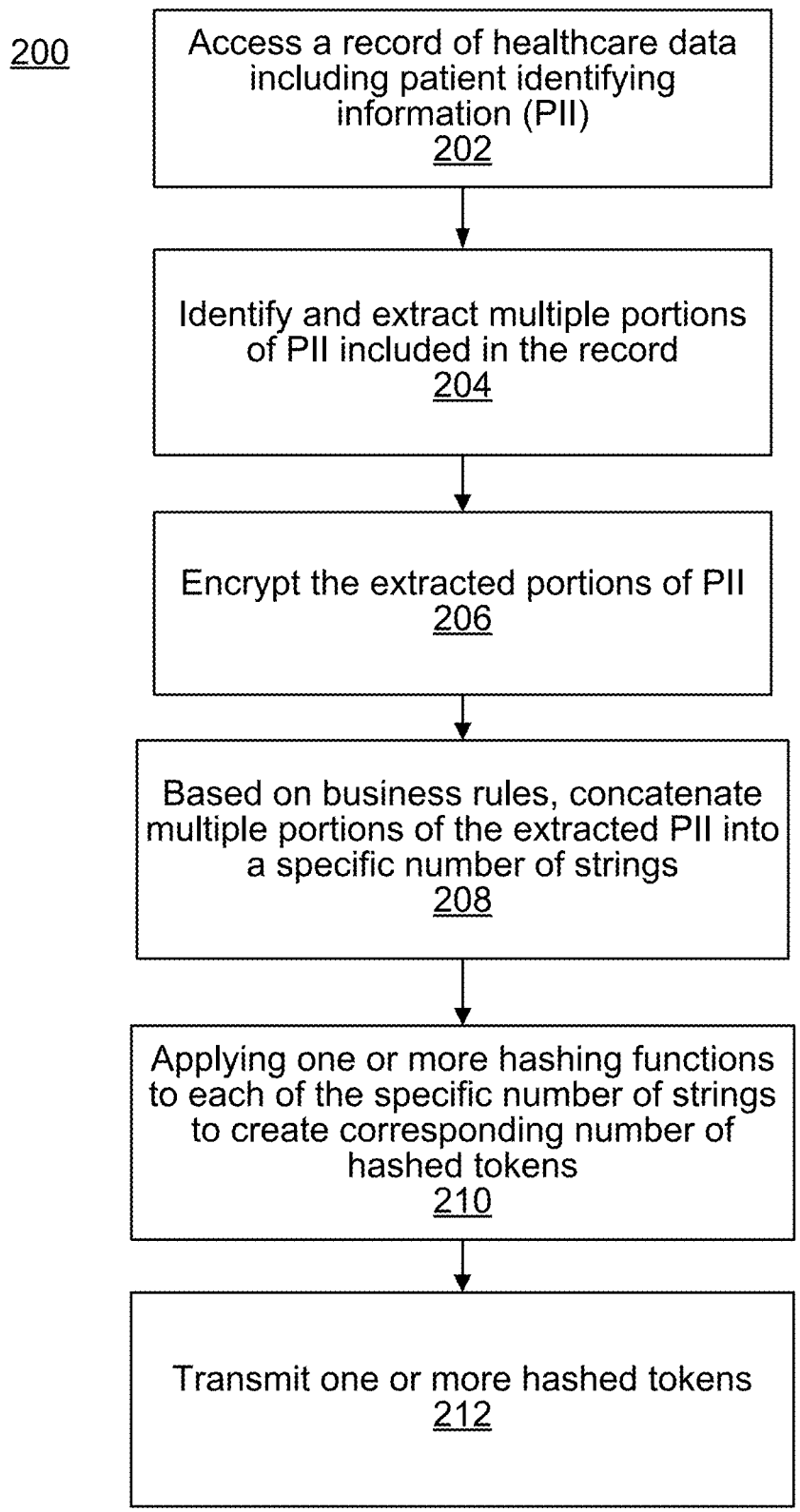
FIG. 2 is a flow chart of an example process for creating one or more anonymous identifier tokens.

The operation of the persistent patient identification system 100 illustrated in FIG. 1 will now be described with regard to FIGS. 2-4. However, the processes described with regard to FIGS. 2-4 may be implemented on any computing system(s) using the same or different modules embodied in software and/or hardware. FIG. 2 is a flow chart of an example process 200 for creating one or more anonymous identifier tokens.

At 202, the data retrieval module 114 accesses a record of healthcare data including patient identifying information (PII). In some implementations, the data retrieval module 114 is configured to access the record of healthcare data from the one or more storage devices 108. Additionally or alternatively, the data retrieval module 114 may be configured to access the record of healthcare data from one or more offsite storage devices and/or to receive the record of healthcare data directly from a user interfacing with the healthcare persistent patient identification system 100 through a user interface.

At 204, the extraction and encryption module 116 is configured to identify and extract multiple portions of PII included in the record. In some implementations, as part of operation 204, the extraction and encryption module 116 is configured to identify a format of the record and utilize business rules specific to the identified format to parse the record and identify the PII. In some implementations, the record of healthcare data may be divided into various fields. Certain fields contained in the record may be of easily identifiable type and format. For example, the record of healthcare data may include first and last name fields, a gender field, a date of birth field, an address field, a physician's name field, and one or more diagnosis fields. These easily identified types of fields may conform to a specific format or rely upon a set of selectable values. Other fields contained in the record may be more difficult to easily classify without knowledge of the record's format. For example, the record of healthcare data may contain one or more text fields that permit a user to enter text in any format. These text fields may include, for example, treatment fields and/or notes fields.

Specific sources of healthcare data records may format records to include a specific set of data fields. In some implementations, these specific sources of records may provide information about the format they utilize for their healthcare data records. Additionally or alternatively, in some implementations, a user or administrator of the persistent patient identification system 100 may review healthcare data records received from these specific sources to analyze and classify the general format of these records. Regardless of the source of formatting information, the persistent patient identification system 100 may be configured to utilize record formatting information along with information about laws, regulations, and rules regarding the protection of PII to designate various portions of a healthcare data record as PII.

In some implementations, the extraction and encryption module 116 may be configured to standardize and format part or all of the healthcare information contained in the accessed record. For example, the extraction and encryption module 116 may be configured to convert part or all of the data contained in the accessed record to UTF-8 format. In another example, the extraction and encryption module 116 may be configured to standardize fields within the healthcare data (e.g., converting text to upper-case).

Moreover, as part of identifying and extracting PII, the extraction and encryption module 116 may be configured to convert certain values to formats that conform with certain rules and regulations governing the handling of PII. For example, in some implementations, the extraction and encryption module 116 may be configured to convert a date of birth contained in the accessed record to an age group so as to obfuscate the actual birth date.

Additionally, as part of identifying PII, the extraction and encryption module 116 may be configured to identify the type and content of the PII included in the data record. In some implementations, for example, the extraction and encryption module 116 may utilize information regarding the overall format of the healthcare data record to determine where in the record certain PII should be located. With information concerning the potential location of PII, the extraction and encryption module 116 may be configured to determine the type of PII actually present in the record and whether the content of the PII is valid. For example, a healthcare data record may include fields for first and last name. The extraction and encryption module 116 may be configured to utilize information regarding the presence and location of the first and last name fields to determine whether the field includes any data (i.e., whether the field is blank) and whether data contained in the field may be a valid first and last name. For example, valid data contained in first and last name fields usually does not contain numbers or certain special characters. Therefore, extraction and encryption module 116 may be configured to analyze the data contained in the first and last name fields to determine whether the data contains any of these impermissible characters, and, if so, designate the data as invalid. In some implementations, the persistent patient identification system 100 only utilizes valid PII for creating the hashed tokens that will be described in greater detail below.

In some implementations, when the extraction and encryption module 116 extracts PII from the healthcare data record, the extraction and encryption module 116 simply creates a copy of the extracted PII, while leaving the PII in the healthcare data record. Alternatively, when the extraction and encryption module 116 extracts PII from the healthcare data record, the extraction and encryption module 116 removes the extracted PII from the healthcare data record. In some implementations, the extraction and encryption module 116 utilizes business rules to determine which portions of PII to extract from the healthcare data record. The business rules may be specific to a geographic region, a type or other classification of the healthcare data record, or the source of the healthcare data record. For example, the business rules may indicate that the laws, rules, or regulations associated with a first geographic region allow certain data that would be considered PII in a second, different geographic region to remain included in a healthcare data record. The identification of the type and content of the PII included in the data record may happen before, during, or after the extraction of the PII from the healthcare data record.

At 206, the extraction and encryption module 116 is configured to encrypt certain portions of the PII. In some implementations, the extraction and encryption module 116 is configured to encrypt each portion of extracted PII individually. In some implementations, the extraction and encryption module 116 may be configured to encrypt a combination of extracted portions of PII. For example, the extraction and encryption module 116 may encrypt a first letter contained in a first name field of a healthcare data record and the entire last name contained in a last name field. In another example, the extraction and encryption module 116 may wait to encrypt the extracted portions of PII until after the creation of one or more strings of PII that will be described with regard to operation 208. The extraction and encryption module 116 may utilize any suitable encryption algorithm or method to encrypt the extract portions of PII. For example, the extraction and encryption module 116 may utilize key-based encryption (e.g., RSA, DSA, or AES), hash function, or any other suitable encryption method. In some implementations, for example, the extraction and encryption module 116 may encrypt one or more of the extracted portions of PII using AES-128.

At 208, the concatenation and hashing module 118 concatenates multiple portions of the extracted PII into a specific number of strings. Ultimately, the concatenation and hashing module 118 creates one or more hashed tokens that may be used by one or more collection-side components 140 to link de-identified healthcare data records. However, the number of hashed tokens may be varied based on a number of different factors. Thus, in some implementations, the concatenation and hashing module 118 is configured to utilize the analysis of the PII contained in the healthcare data record performed by the extraction and encryption module 116 in conjunction with one or more business rules to determine how many concatenated strings of extracted PII (and ultimately hashed tokens) to create.

In some implementations, the one or more business rules utilized by the concatenation and hashing module 118 may be specific to a geographic region. Thus, depending on a geographic region associated with the healthcare data record and/or the persistent patient identification system 100, the one or more business rules may indicate that a certain number of strings of extracted PII should be created. Additionally or alternatively, the one or more business rules may indicate that the laws, rules, or regulations associated with a geographic region require that healthcare data records always include certain PII. As a result, the one or more business rules may indicate that the number of strings of extracted PII can be fewer, since all healthcare data records within the region will uniformly include a certain amount of PII, making it more likely that the created hashed tokens can be used to accurately link de-identified records.

In some implementations, the one or more business rules by the concatenation and hashing module 118 may define a relationship between the amount, type, and content of PII included in a healthcare data record and the number of strings of extracted PII to be created. For example, certain PII (e.g., social security number or healthcare insurance number) is very accurate in identifying a person, while other PII (e.g., zip code or age group) are unlikely to uniquely identify an individual, though they may be useful in narrowing a potential group of matching persons. The greater the amount of PII that is included in a healthcare data record, the more likely that two healthcare data records with the same PII are matches. Unfortunately, given the great number of possible sources of healthcare data records and the great number of potential formats a healthcare data record might take, the amount of PII included in any one healthcare record may vary. Moreover, where a healthcare data record only includes (or regional laws, rules, or regulations only permit consideration of) PII that can narrow a group of potential persons but not uniquely identify them, it can be helpful to consider as much PII as possible to increase the statistical likelihood of matching two de-identified healthcare data records. Accordingly, the amount, type, and content of PII included in a healthcare data record may increase or decrease a number of strings to be generated in order to satisfy a statistical likelihood of matching de-identified patient records.

The concatenation and hashing module 118 also utilizes one or more business rules to determine which extracted PII to include in each concatenated string and in which order. As with the number of concatenated strings to be created, the business rules indicating the content and ordering of the strings of extracted PII are generally designed to increase the statistical likelihood that the resulting hashed tokens can be matched with hashed tokens associated with other healthcare data records related to the same person(s). In one example, the concatenation and hashing module 118 may utilize the one or more business rules and the analysis of the PII performed by the extraction and encryption module 116 to determine that two strings should be created for a particular healthcare data record. The one or more business rules may indicate that a first string should include encrypted versions of the person's last name, date of birth, and zip code, and that a second string should include encrypted versions of the person's first name, last name, and insurance provider. Of course, the number of strings to be created and the ordering and content of the strings can be varied in any way.

The source-side component 102 may perform operations 204, 206, and 208 in many different ways. For example, the details of the one or more business rules relied upon in each operation may vary depending on a number of factors (e.g., geographic region, type of healthcare data record, details regarding the person(s) to whom the healthcare data record relates, etc.). In one example of token creation, the concatenation and hashing module 118 accesses one or more business rules specific to a geographical region associated with the healthcare data record or the healthcare persistent patient identification system 100. The concatenation and hashing module 118 utilizes the one or more accessed business rules to extract and analyze multiple portions of PII included in the record. As described above, the process of extraction and analysis may include identifying an amount, type, and content of PII included in a healthcare data record.

In this example of token creation, based on the one or more business rules and the analysis of the extracted portions of PII, the concatenation and hashing module 118 may determine a number concatenated strings to create. The number of strings of concatenated PII may vary depending on the type and the content of the PII included in the record of healthcare data. For example, the relationship between the number of concatenated strings and the type and the content of the PII included in the record of healthcare data indicates that the number of concatenated strings is greater when certain types of PII are not included in the record than when the certain types of PII are included in the record.

In this example of token creation, the extraction and encryption module 116 individually encrypts each of the extracted portions of PII. As described above, the extraction and encryption module 116 may utilize any suitable encryption algorithm or method to encrypt the extract portions of PII. The concatenation and hashing module 118 may utilize one or more business rules to concatenate a plurality of the encrypted portions of PII into the determined number of concatenated strings. In some implementations, the one or more business rules indicate which encrypted portions of PII to concatenate into each string and an ordering of the encrypted portions of PII within each string. As described above, these business rules may be specific to a geographic region.

At 210, the concatenation and hashing module 118 is configured to apply one or more hashing functions to each of the specific number of strings to create a corresponding number of hashed tokens. The number and type of hashing functions used by the concatenation and hashing module 118 to hash each of the concatenated strings of PII may vary. Moreover, another cryptographic primitive, such as a block cipher, can be used instead of a hashing function. However, the hash function may be preferred because it generally has no inverse function that can recover the input from the hash function's output. A hash function maps a bit string of arbitrary length to another bit string of fixed length. Hash functions include Ripe-MD, Whirlpool, Haval, MD4, MD5, and the SHA group of hash functions. Preferably, the concatenation and hashing module 118 utilizes the SHA-2 family, in particular, SHA-256 which creates 256 bit hashes. The SHA family of hash functions was designed by the National Institute of Standards and Technology and is a Federal Information Processing Standard, as described by Federal Information Processing Standards Publication 180-2, dated Aug. 1, 2002. Federal Information Processing Standards Publication 180-2 also provides an algorithm and examples for implementing an SHA-256 hash function.

In some implementations, the concatenation and hashing module 118 may be configured to apply multiple hashing functions to each of the concatenated strings of PII. For example, in some implementations, the concatenation and hashing module 118 may, for each of the concatenated strings of PII, append a portion of an encryption key to the concatenated string. The concatenation and hashing module 118 may then create an intermediary token by applying a first hashing function (e.g., SHA-256) to the concatenated string with the appended portion of the encryption key. The concatenation and hashing module 118 may then append another portion of the encryption key to the intermediary token. The concatenation and hashing module 118 may then create a final hashed token by applying a second hashing function (e.g., SHA-256) to the intermediary token with the appended other portion of the encryption key.

At 212, the transmission/reception module 124 is configured to store the specific number of hashed tokens created in operation 210 in association with the healthcare data record(s) from which the PII was extracted. In some implementations, the transmission/reception module 124 is configured to store the specific number of hashed tokens with the healthcare data record. In some implementations, the transmission/reception module 124 is configured to store the specific number of hashed tokens separately from the healthcare data record and link them together through known linking techniques.

In some implementations, the transmission/reception module 124 is configured to store a PII presence indicator along with either or both of the hashed tokens and the de-identified healthcare data record. The PII presence indicator indicates which types of PII are contained in each token. For example, the business rules may indicate that a particular hashed token created for a record of healthcare data should be based on the last name field, the postal code field, and the age field included in the record of healthcare data. However, the record of healthcare data may not include the last name field or it may otherwise be determined to be invalid. In such an instance, the concatenation and hashing module 118 may be configured to use a preset NULL value in place of the last name field when creating the hashed token. In such a case the PII presence indicator will indicate that the last name field will indicate that the last name field was not present in the original record. The PII presence indicator may then be used, for example, by the collection-side component 140 when attempting to link de-identified patient records and/or determine a matching indexing tag.

Moreover, in some implementations, the transmission/reception module 124 is configured to transmit the specific number of hashed tokens separately and the de-identified healthcare data record to another location or computer system, such as the collection-side component 140. The transmission module 126 may utilize any known forms of storage (e.g., RAM, ROM, optical drive, etc.), transmission method (e.g., e-mail, SFTP, etc.), and transmission medium (wired, wireless, etc.).

Figure 3:
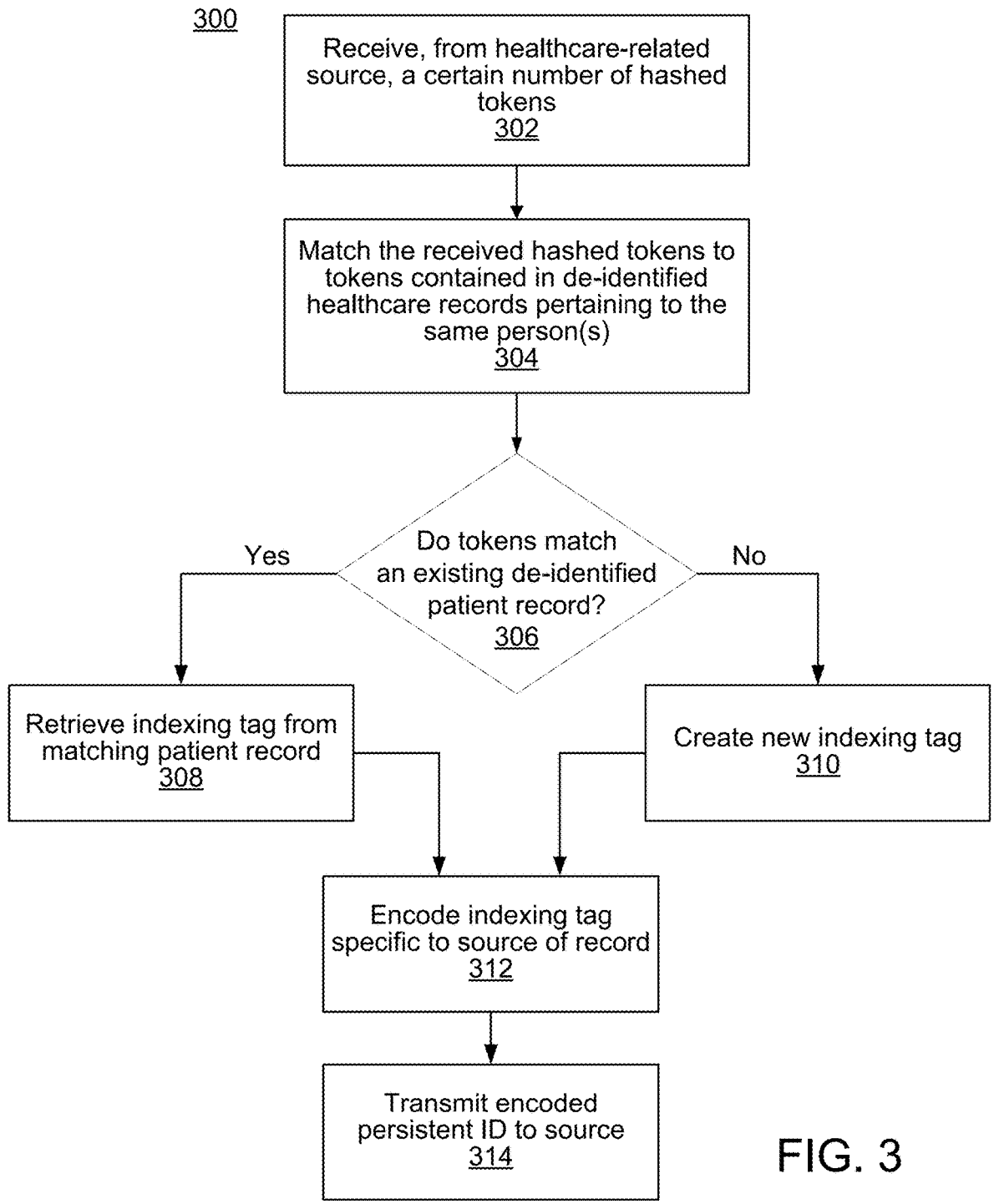
FIG. 3 is a flow chart of an example process for converting one or more anonymous identifier tokens into a source-specific, persistent patient identifier.

FIG. 3 is a flow chart of an example process 300 for converting one or more anonymous identifier tokens into a source-specific, persistent patient identifier. For purposes of illustration, the process 400 will be described with regard to collection-side component 140. However, any computing system(s) can be utilized to perform the described functions.

At 302, the data reception module 142 of a collection-side component 140 receives, from a source-side component 102, one or more hashed tokens. These hashed tokens may be created by the process 200 described above with regard to FIG. 2 or may be created by any other suitable process. In some implementations, the hashed tokes and/or an associated de-identified healthcare record are encrypted before being transmitted to the collection-side component 140. In such implementations, the pre-processing module 144 decrypts the encrypted de-identified healthcare record and the certain number of hashed tokens. Importantly, the decryption performed by the pre-processing module 144 is only with regard to the transmission layer of encryption utilized by the source-side component 140, not with regard to any of the obfuscation utilized to create the hashed tokens themselves. Moreover, the pre-processing module 144 may be configured to otherwise parse and/or prepare the information received from the collection-side component 140 for use by other modules of the source-side component 140.

At 304, the identifier management module 146 compares the received one or more hashed tokens with other hashed tokens associated with previously processed de-identified healthcare records. The identifier management module 146 attempts to find the most likely match between the received one or more hashed tokens and the previously received hashed tokens in order to link de-identified healthcare records that correspond to the same person(s). In some implementations, de-identified healthcare records that correspond to the same person(s) are stored in association with an anonymous profile corresponding to the person(s). Moreover, as described above, in some implementations, the de-identified healthcare records that correspond to the same person(s) are stored in association with an indexing tag that anonymously identifies the person(s).

At 306, the identifier management module 146 determines whether the received one or more hashed tokens match other hashed tokens associated with previously processed de-identified healthcare records. If there is a match, at 308, the identifier management module 146 retrieves an indexing tag associated with the previously processed de-identified healthcare records. Alternatively, if there is not a match, at 310, the identifier management module 146 may be configured to create a new indexing tag and stores the new indexing tag in association with the received one or more hashed tokens.

At 312, the identifier management module 146 encodes or encrypts the retrieved or newly created indexing tag in a manner specific to the source of the received one or more hashed tokens, creating a source-specific, persistent patient identifier. For example, if the received one or more hashed tokens are received from a particular health insurance company, the encodes or encrypts the retrieved or newly created indexing tag in a manner specific to that particular health insurance company such that no other health insurance company (or any other unrelated healthcare professional or organization) can utilize the source-specific, persistent patient identifier with regard to its own stored data.

The identifier management module 146 may be configured to encode or encrypt the retrieved or newly created indexing tag using any suitable process and/or algorithm. For example, the identifier management module 146 may be configured to use a hashing function to encode the retrieved or newly created indexing tag. In some implementations, the hashing function may be specific to the source of the received one or more hashed tokens. Additionally or alternatively, the retrieved or newly created indexing tag may be combined with other data (e.g., a key) specific to the source of the received one or more hashed tokens and then encoded (e.g., by using one or more hashing functions).

At 314, the ID transmission module 148 transmits the source-specific, persistent patient identifier (i.e., the encoded/encrypted indexing tag) to the source of the received one or more hashed tokens. In some implementations, the ID transmission module 148 transmits the source-specific, persistent patient identifier to the source of the received one or more hashed tokens in a response-type message format that indicates to the source of the received one or more hashed tokens that the source-specific, persistent patient identifier is associated with the received one or more hashed tokens. Additionally or alternatively, the ID transmission module 148 transmits the source-specific, persistent patient identifier with other information (e.g., a health plan identifier) that facilitates a matching of the source-specific, persistent patient identifier with the patient's records at the source.

Figure 4:
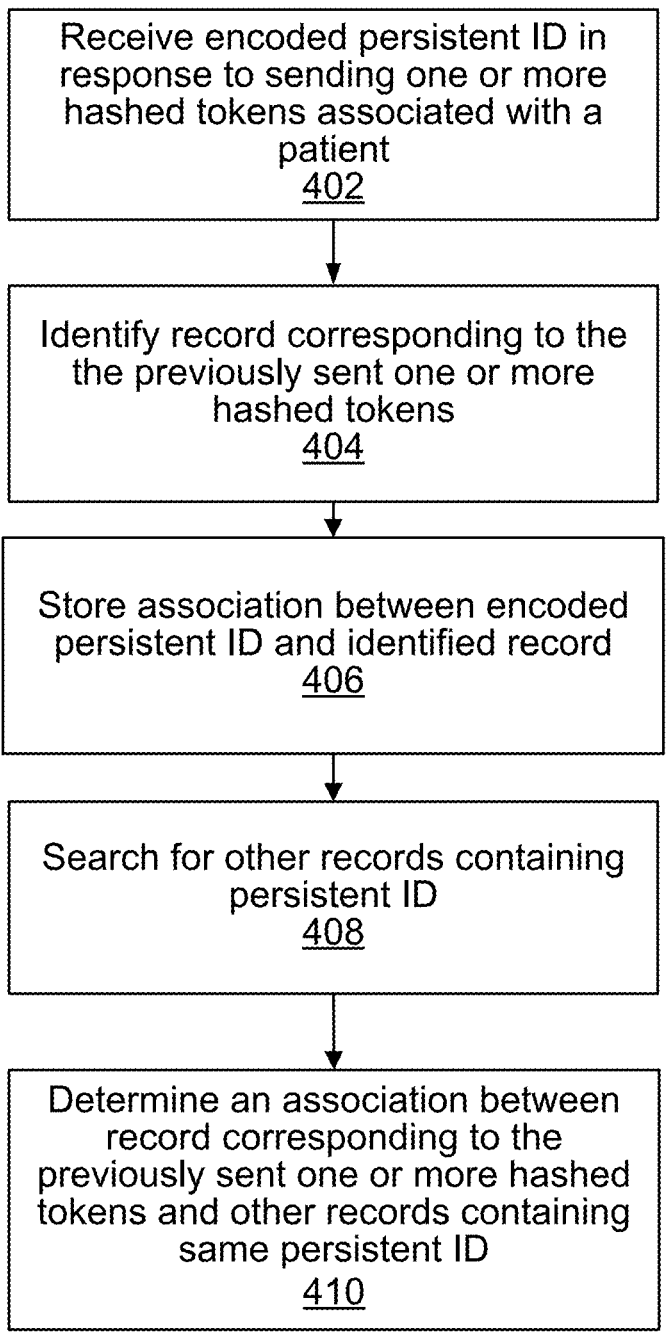
FIG. 4 is a flow chart of an example process for determining associations between records sharing the same source-specific, persistent patient identifier.

FIG. 4 is a flow chart of an example process 400 for process for determining associations between records sharing the same source-specific, persistent patient identifier. For purposes of illustration, the process 400 will be described with regard to collection-side component 140. However, any computing system(s) can be utilized to perform the described functions.

At 402, the transmission/reception module 124 of a source-side component 102 receives a source-specific, persistent patient identifier from a collection-side component 140. The received source-specific, persistent patient identifier corresponds to a record that resulted in the creation of the one or more hashed tokens sent by the source-side component 102 or by another system on behalf of the source-side component 102 (e.g., a patient management hub). In some implementations, the source-specific, persistent patient identifier is encrypted before being transmitted to the source-side component 102. In such implementations, the transmission/reception module 124 decrypts the encrypted de-identified healthcare record and the certain number of hashed tokens.

As described above with regard to FIG. 3, the source-side component 102 either receives the source-specific, persistent patient identifier in a response-type message or with other identifying information, thereby allowing the source-side component 102 to correlate the received source-specific, persistent patient identifier with the record from which the previously sent one or more hashed tokens were created. Accordingly, at 404, the association module 126 identifies the patient record corresponding to the previously sent one or more hashed tokens. For example, in an implementation where the source-side component 102 is implemented by or on behalf a health insurance company, the association module 126 may match the received source-specific, persistent patient identifier with the record from which the previously sent one or more hashed tokens were created using a health plan identifier associated with the record from which the one or more hashed tokens were created.

At 406, the association module 126 stores an association between the received source-specific, persistent patient identifier and the record from which the one or more hashed tokens were created. For example, in an implementation where the source-side component 102 is implemented by or on behalf a health insurance company, the association module 126 may store an association between the received source-specific, persistent patient identifier and a health plan identifier associated with the record from which the one or more hashed tokens were created.

At 408, association module 126 searches for other records that may contain a copy of the received source-specific, persistent patient identifier. The association module 126 may implement any suitable searching and/or matching algorithms for this purpose.

If one or more other records are found to store an association with the same source-specific, persistent patient identifier, at 410, the association module 126 determines and stores an association between the record from which the above-described one or more hashed tokens were created and the one or more other identified records. In an implementation where the source-side component 102 is implemented by or on behalf a health insurance company and the one or more other records are associated with a different health plan identifier, the association module 126 may be configured to associated the health plan identifier from the record from which the above-described one or more hashed tokens were created with the different health plan identifier contained in the one or more other records found by the association module 126 in operation 408. In so doing, the association module 126 allows the health insurance company to track a patient for whom it has previously stored records, even though the patient has changed health plans and is now associated with a new health plan identifier.

Though FIG. 4 has primarily been described with regard to an example in which the source-side component 102 is implemented by or on behalf a health insurance company and the records are associated with health insurance plans, the above-described process 400 is equally applicable to other health (or non-health) related professionals or organizations that desire to track patients or other types of users even after certain identifying information associated with the patient or user has changed.

Figure 5:
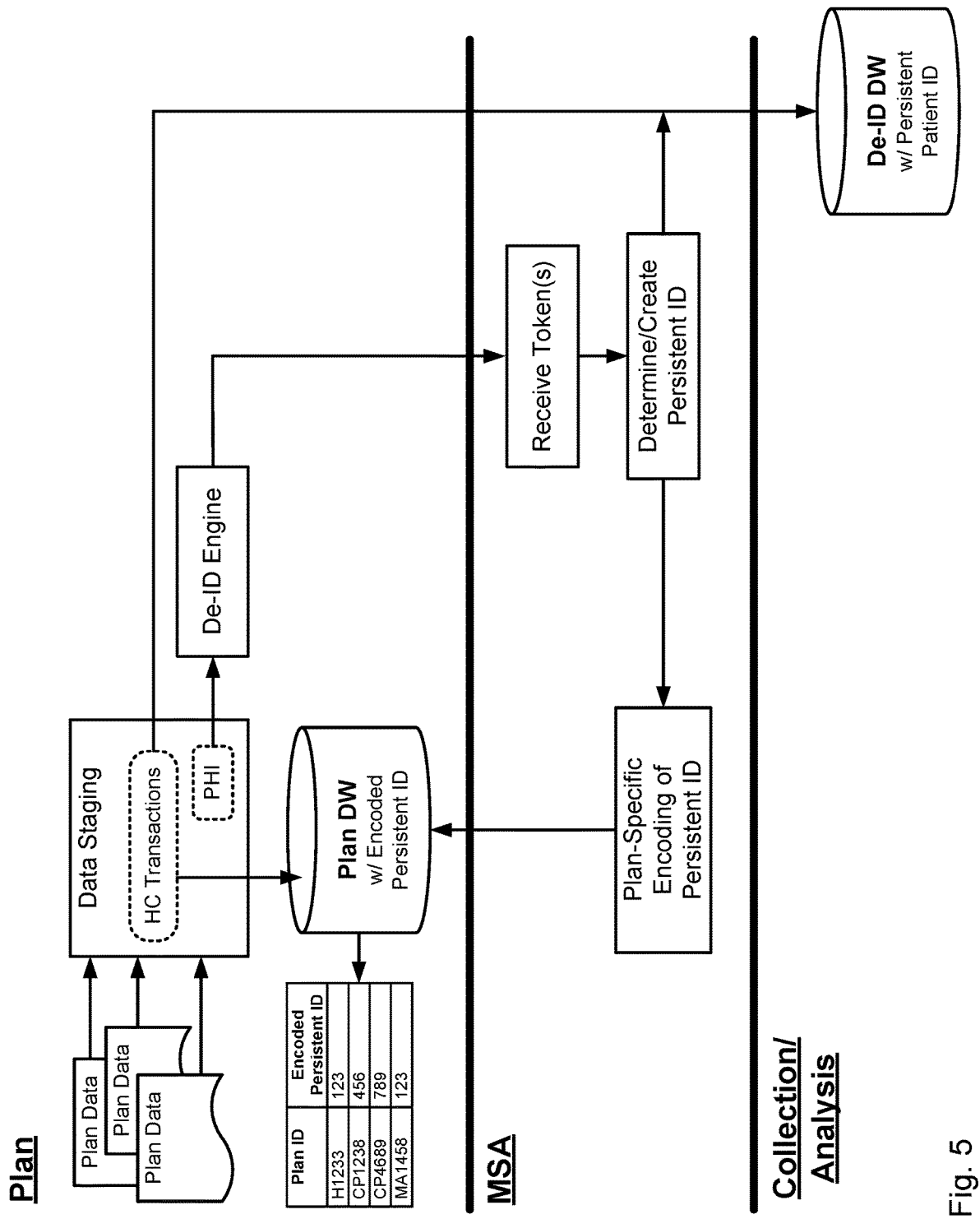
FIG. 5 is an example implementation of a system for source-specific, persistent patient identifiers.

FIG. 5 is an example implementation of a system 500 for source-specific, persistent patient identifiers. For purposes of illustration, the system 500 will be described with regard to the implementations illustrated in and previously describe with regard to FIGS. 1-4. However, any computing system(s) and/or processes can be utilized to perform the described functions. Moreover, the system 500 will be described with regard to a specific health insurance organization, but the system 500 is equally applicable to other health-related professionals or organizations (or non-health-related organizations), as described previously.

In system 500, a health insurance organization (i.e. a "plan") may have plan data for many different patients across many different types of plans. For each transaction associated with a patient who has or is requesting an insurance plan with the health insurance organization (e.g., a claim or an application for insurance), the health insurance organization may store the record in a plan-related data warehouse. In addition, the may also de-identify the record may using the process 200 or a similar process for transmission to trusted third party intermediaries (i.e. "MSA") and/or one or more sites that collect and analyze de-identified healthcare data (i.e., "Collection/Analysis"). The MSA and/or Collection/Analysis organizations may each implement all or a portion of the collection-side system described above with regard to FIGS. 1 and 3.

In some implementations, as part of the process 200, the health insurance organization sends one or more hashed tokens to the MSA. The MSA utilizes the process 300 described with regard to FIG. 3 or a similar process to create a source-specific, patient identifier. As part of this process 300, the MSA encodes or encrypts the source-specific, patient identifier in a manner specific to the health insurance organization so as to protect the privacy of the patient. The MSA then transmits the source-specific, persistent patient identifier back to the health insurance organization. Additionally, in some implementations, the MSA and/or the health insurance organization transmits the one or more hashed tokens and/or the indexing tag to a Collection/Analysis organization. By transmitting only an indexing tag instead of the one or more hashed tokens to the Collection/Analysis organization, this example configuration of the MSA may further protect patient privacy by ensuring that no third-party entity (e.g., the MSA or the Collection/Analysis organization) has access to both the hashed tokens and the de-identified patient record, since the health insurance organization may further be configured to transmit the de-identified patient record directly to the Collection/Analysis organization.

In some implementations, the health insurance organization stores source-specific, persistent patient identifier in association with the record from which the one or more hashed tokens were created. Additionally, in accordance with process 400, the health insurance organization may attempt to match the source-specific, persistent patient identifier with other records in order to track patients as the patient transitions between insurance plans that may have different plan identifier.

Implementations of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non-transitory program carrier for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example a programmable processor, a computer, or multiple processors or computers. The apparatus can also be or further include special purpose logic circuitry, e.g., a central processing unit (CPU), a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example Linux, UNIX, Windows, Mac OS, Android, iOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a central processing unit (CPU), a FPGA (field programmable gate array), or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN), a wide area network (WAN), e.g., the Internet, and a wireless local area network (WLAN).

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

The invention claimed is:

1. A method comprising:
receiving, from a healthcare related source, one or more hashed tokens, each hashed token based on a record of healthcare data;
comparing the received one or more hashed tokens to one or more other tokens contained in corresponding de-identified healthcare records pertaining to a respective person;
in response to determining that one or more matches exist between the received one or more hashed tokens and a subset of the one or more other tokens, identifying the corresponding de-identified health records for the subset of the one or more other tokens and an indexing tag associated with the corresponding de-identified health records;
generating, for each identified indexing tag, a source-specific, persistent patient identifier by encrypting the corresponding indexing tag with a computing rule specific to the healthcare related source that provided the received one or more hashed tokens, wherein the computing rule is based on patient identifying information (PII) extracted from the record of healthcare data; and
transmitting each of the source-specific, persistent patient identifiers to the healthcare related source of the received one or more hashed tokens.

2. The method of claim 1, wherein receiving the one or more hashed tokens comprises:
accessing, by the healthcare related source, a record of healthcare data, wherein the record comprises patient identifying information (PII) associated with one or more persons to whom the healthcare data pertains;
extracting, by the healthcare related source, portions of PII in the accessed record of healthcare data;
encrypting, by the healthcare related source, the extracted portions of PII;
generating, by the healthcare related source, the one or more hashed tokens to the extracted portions of PII; and
transmitting, by the healthcare related source, the one or more hashed tokens to a collection-side system.

3. The method of claim 1, wherein comparing the received one or more hashed tokens to the one or more other tokens contained in de-identified healthcare records pertaining to the person further comprises:
obtaining one or more previously received hashed tokens;
comparing the received one or more hashed tokens to the one or more previously received hashed tokens; and
determining that a match exists between the received one or more hashed tokens to at least one of the one or more previously received hashed tokens, wherein the match indicates a link between tokens indicative of the person.

4. The method of claim 3, wherein in response to determining that the match does exist between the received one or more hashed tokens and de-identified health records, retrieving the indexing tag associated with the matched de-identified health records further comprises:

retrieving the de-identified health records corresponding to the matched previously received hashed tokens; and retrieving the indexing tag associated with the matched de-identified health records associated with the matched previously received hashed tokens.

5. The method of claim 1, wherein generating the source-specific, persistent patient identifier by encrypting indexing tag to a source of the received one or more hashed tokens further comprises:

encrypting the indexing tag to the source of the received one or more hashed tokens, wherein the source of the received one or more hashed tokens corresponds to a healthcare related source such that the encrypted indexing tag is inaccessible to other healthcare related sources.

6. The method of claim 1, wherein transmitting the source-specific, persistent patient identifier to the healthcare related source of the received one or more hashed tokens further comprises:

generating a message that comprises (i) the source-specific, persistent patient identifier, (ii) an indication that the source-specific, persistent patient identifier is associated with the received one or more hashed tokens, and (iii) an identifier of the healthcare related source; and transmitting the message to the healthcare related source.

7. The method of claim 1, comprising:

determining health care data previously processed at a collection-side system does not match to data for a healthcare record received from a source-side system;

generating a new indexing tag to anonymously identify a patient that corresponds to the data for the healthcare record; and storing the data for the healthcare record in association with the new indexing tag.

8. A system comprising:

one or more computers and one or more storage devices storing instructions that are operable, when executed by the one or more computers, to cause the one or more computers to perform operations comprising:

receiving, from a healthcare related source, one or more hashed tokens, each hashed token based on a record of healthcare data;

comparing the received one or more hashed tokens to one or more other tokens contained in corresponding de-identified healthcare records pertaining to a respective person;

in response to determining that one or more matches exist between the received one or more hashed tokens and a subset of the one or more other tokens, identifying the corresponding de-identified health records for the subset of the one or more other tokens and an indexing tag associated with the corresponding de-identified health records;

generating, for each identified indexing tag, a source-specific, persistent patient identifier by encrypting the corresponding indexing tag with a computing rule specific to the healthcare related source that provided the received one or more hashed tokens, wherein the computing rule is based on patient identifying information (PII) extracted from the record of healthcare data; and transmitting each of the source-specific, persistent patient identifiers to the healthcare related source of the received one or more hashed tokens.

9. The system of claim 8, wherein receiving the one or more hashed tokens comprises:

accessing, by the healthcare related source, a record of healthcare data, wherein the record comprises patient identifying information (PII) associated with one or more persons to whom the healthcare data pertains;

extracting, by the healthcare related source, portions of PII in the accessed record of healthcare data;

encrypting, by the healthcare related source, the extracted portions of PII;

generating, by the healthcare related source, the one or more hashed tokens to the extracted portions of PII; and transmitting, by the healthcare related source, the one or more hashed tokens to a collection-side system.

10. The system of claim 8, wherein comparing the received one or more hashed tokens to the one or more other tokens contained in de-identified healthcare records pertaining to the person further comprises:

obtaining one or more previously received hashed tokens;

comparing the received one or more hashed tokens to the one or more previously received hashed tokens; and determining that a match exists between the received one or more hashed tokens to at least one of the one or more previously received hashed tokens, wherein the match indicates a link between tokens indicative of the person.

11. The system of claim 10, wherein in response to determining that the match does exist between the received one or more hashed tokens and de-identified health records, retrieving the indexing tag associated with the matched de-identified health records further comprises:

retrieving the de-identified health records corresponding to the matched previously received hashed tokens; and retrieving the indexing tag associated with the matched de-identified health records associated with the matched previously received hashed tokens.

12. The system of claim 8, wherein generating the source-specific, persistent patient identifier by encrypting the indexing tag to a source of the received one or more hashed tokens further comprises:

encrypting the indexing tag to the source of the received one or more hashed tokens, wherein the source of the received one or more hashed tokens corresponds to a healthcare related source such that the encrypted indexing tag is inaccessible to other healthcare related sources.

13. The system of claim 8, wherein transmitting the source-specific, persistent patient identifier to the healthcare related source of the received one or more hashed tokens further comprises:

generating a message that comprises (i) the source-specific, persistent patient identifier, (ii) an indication that the source-specific, persistent patient identifier is associated with the received one or more hashed tokens, and (iii) an identifier of the healthcare related source; and transmitting the message to the healthcare related source.

14. The system of claim 8, comprising:

determining health care data previously processed at a collection-side system does not match to data for a healthcare record received from a source-side system;

generating a new indexing tag to anonymously identify a patient that corresponds to the data for the healthcare record; and storing the data for the healthcare record in association with the new indexing tag.

15. A non-transitory computer-readable medium storing software comprising instructions executable by one or more computers which, upon such execution, cause the one or more computers to perform operations comprising:

receiving, from a healthcare related source, one or more hashed tokens, each hashed token based on a record of healthcare data;

comparing the received one or more hashed tokens to one or more other tokens contained in corresponding de-identified healthcare records pertaining to a respective person;

in response to determining that one or more matches exist between the received one or more hashed tokens and a subset of the one or more other tokens, identifying the corresponding de-identified health records for the subset of the one or more other tokens and an indexing tag associated with the corresponding de-identified health records;

generating, for each identified indexing tag, a source-specific, persistent patient identifier by encrypting the corresponding indexing tag with a computing rule specific to the healthcare related source that provided the received one or more hashed tokens, wherein the computing rule is based on patient identifying information (PII) extracted from the record of healthcare data; and transmitting each of the source-specific, persistent patient identifiers to the healthcare related source of the received one or more hashed tokens.

16. The non-transitory computer-readable medium of claim 15, wherein receiving the one or more hashed tokens comprises:

accessing, by the healthcare related source, a record of healthcare data, wherein the record comprises patient identifying information (PII) associated with one or more persons to whom the healthcare data pertains;

extracting, by the healthcare related source, portions of PII in the accessed record of healthcare data;

encrypting, by the healthcare related source, the extracted portions of PII;

generating, by the healthcare related source, the one or more hashed tokens to the extracted portions of PII; and transmitting, by the healthcare related source, the one or more hashed tokens to a collection-side system.

17. The non-transitory computer-readable medium of claim 15, wherein comparing the received one or more hashed tokens to the one or more other tokens contained in de-identified healthcare records pertaining to the person further comprises:

obtaining one or more previously received hashed tokens;

comparing the received one or more hashed tokens to the one or more previously received hashed tokens; and determining that a match exists between the received one or more hashed tokens to at least one of the one or more previously received hashed tokens, wherein the match indicates a link between tokens indicative of the person.

18. The non-transitory computer-readable medium of claim 17, wherein in response to determining that the match does exist between the received hashed token and de-identified health records, retrieving the indexing tag associated with the matched de-identified health records further comprises:

retrieving the de-identified health records corresponding to the matched previously received hashed tokens; and retrieving the indexing tag associated with the matched de-identified health records associated with the matched previously received hashed tokens.

19. The non-transitory computer-readable medium of claim 15, wherein generating the source-specific, persistent patient identifier by encrypting the indexing tag to a source of the received one or more hashed tokens further comprises:

encrypting the indexing tag to the source of the received one or more hashed tokens, wherein the source of the received one or more hashed tokens corresponds to a healthcare related source such that the encrypted indexing tag is inaccessible to other healthcare related sources.

20. The non-transitory computer-readable medium of claim 15, wherein transmitting the source-specific, persistent patient identifier to the healthcare related source of the received one or more hashed tokens further comprises:

generating a message that comprises (i) the source-specific, persistent patient identifier, (ii) an indication that the source-specific, persistent patient identifier is associated with the received one or more hashed tokens, and (iii) an identifier of the healthcare related source; and transmitting the message to the healthcare related source.

21. The method of claim 1, wherein receiving, from the healthcare related source, the one or more hashed tokens comprises receiving, from the healthcare related source, the one or more hashed tokens and data indicating types of patient identifying information (PII) in each of the one or more hashed tokens.

22. The method of claim 21, wherein comparing the received one or more hashed tokens to one or more other hashed tokens comprises comparing, using the data indicating the types of PII, the received one or more hashed tokens to the one or more other tokens contained in the corresponding de-identified healthcare records pertaining to the respective person.

\* \* \* \* \*